United States Patent
Lee et al.

(10) Patent No.: US 9,914,984 B2
(45) Date of Patent: Mar. 13, 2018

(54) COMPOSITION FOR EPIMERIZATION OF NON-PHOSPHORYLATED HEXOSE COMPRISING SUGAR EPIMERASES DERIVED FROM THERMOPHILES

(71) Applicant: CJ CheilJedang Corporation, Seoul (KR)

(72) Inventors: Dong Woo Lee, Daegu (KR); Sun Mi Shin, Daejeon (KR); Yong Jik Lee, Daegu (KR); Sang Jae Lee, Daegu (KR)

(73) Assignee: CJ CheilJedang Corporation, Seoul (KR)

( * ) Notice: Subject to any disclaimer, the term of this patent is extended or adjusted under 35 U.S.C. 154(b) by 0 days.

(21) Appl. No.: 15/037,274

(22) PCT Filed: Nov. 19, 2014

(86) PCT No.: PCT/KR2014/011139
§ 371 (c)(1),
(2) Date: May 17, 2016

(87) PCT Pub. No.: WO2015/076563
PCT Pub. Date: May 28, 2015

(65) Prior Publication Data
US 2016/0295891 A1    Oct. 13, 2016

(30) Foreign Application Priority Data
Nov. 19, 2013   (KR) .................. 10-2013-0140546

(51) Int. Cl.
| | |
|---|---|
| C12P 7/26 | (2006.01) |
| C12P 19/24 | (2006.01) |
| C12P 19/02 | (2006.01) |
| C12N 9/90 | (2006.01) |
| C07H 21/04 | (2006.01) |
| A23L 29/30 | (2016.01) |
| A23L 27/30 | (2016.01) |

(52) U.S. Cl.
CPC ....... *C12Y 501/03002* (2013.01); *A23L 27/33* (2016.08); *A23L 29/30* (2016.08); *C12N 9/90* (2013.01); *C12P 19/02* (2013.01); *C12P 19/24* (2013.01); *C12Y 501/03* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2010/0190225 A1* | 7/2010 | Oh | C12N 9/90 435/148 |
| 2012/0329098 A1 | 12/2012 | Watanabe et al. | |

OTHER PUBLICATIONS

Whisstock et al. Quaterly Reviews of Biophysics, 2003, "Prediction of protein function from protein sequence and structure", 36(3): 307-340.*

Witkowski et al. Conversion of a beta-ketoacyl synthase to a malonyl decarboxylase by replacement of the active-site cysteine with glutamine, Biochemistry. Sep. 7, 1999;38(36):11643-50.*

Kisselev L., Polypeptide release factors in prokaryotes and eukaryotes: same function, different structure. Structure, 2002, vol. 10:8-9.*

Sakuraba et al. "Structure of a D-tagatose 3-epimerase-related protein form the hyperthermophilic bacterium Thermotoga maritima", Acta Crystallographica, Section F, Structural Biology and Crystallization Communications, Feb. 14, 2009, vol. 65, Pt. No. 3, pp. 199-203.

* cited by examiner

*Primary Examiner* — Iqbal H Chowdhury
(74) *Attorney, Agent, or Firm* — Bret E. Field; Bozicevic, Field & Francis LLP

(57) ABSTRACT

The present invention relates to a composition for epimerization of a non-phosphorylated hexose, comprising sugar epimerases derived from thermophiles, and a method for preparing a non-phosphorylated hexose epimer using the composition. The sugar epimerases derived from thermophiles according to the present invention can effectively catalyze an epimerization reaction of a non-phosphorylated hexose and can easily produce an epimer form of the non-phosphorylated hexose, in particular a rare sugar hexose, and thus can be usefully utilized in the pharmaceutical and food industry.

7 Claims, 7 Drawing Sheets

[Fig. 1]
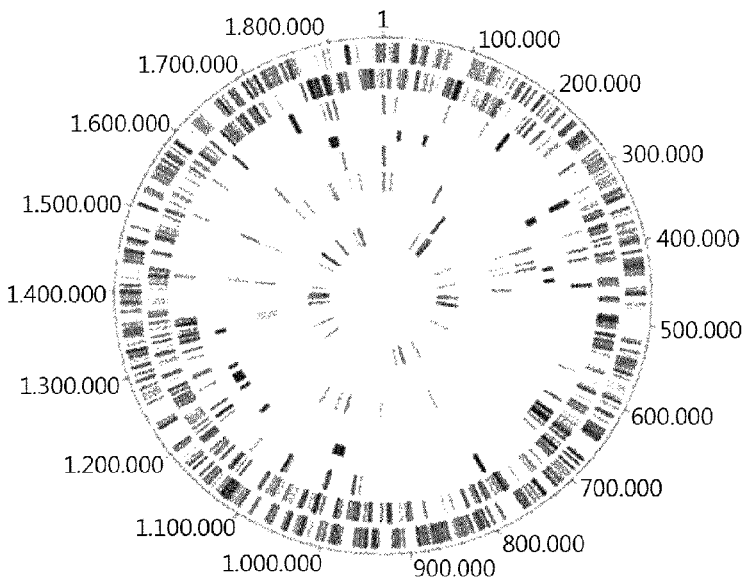
*Thermotoga maritima* MSB8
1. Aldose-1 epimerase (1,071 bp) A1E/ Gene ID : 897200, Gene symbol : TM0282
2. UDP-N-acetylglucosamine-2 epimerase (1,137 bp) G2E / Gene ID : 897719, Gene symbol : TM1034
3. D-tagatose-3 epimerase (813 bp) T3E / Gene ID :897418, Gene symbol : TM0416
4. UDP-glucose-4 epimerase (930 bp) G4E/ Gene ID : 897553, Gene symbol : TM0509
*Caldanaerobacter yonseiensis* KB-1
1. D-tagaturonate epimerase (1,452 bp) / Gene symbol : CYTE

[Fig. 2]
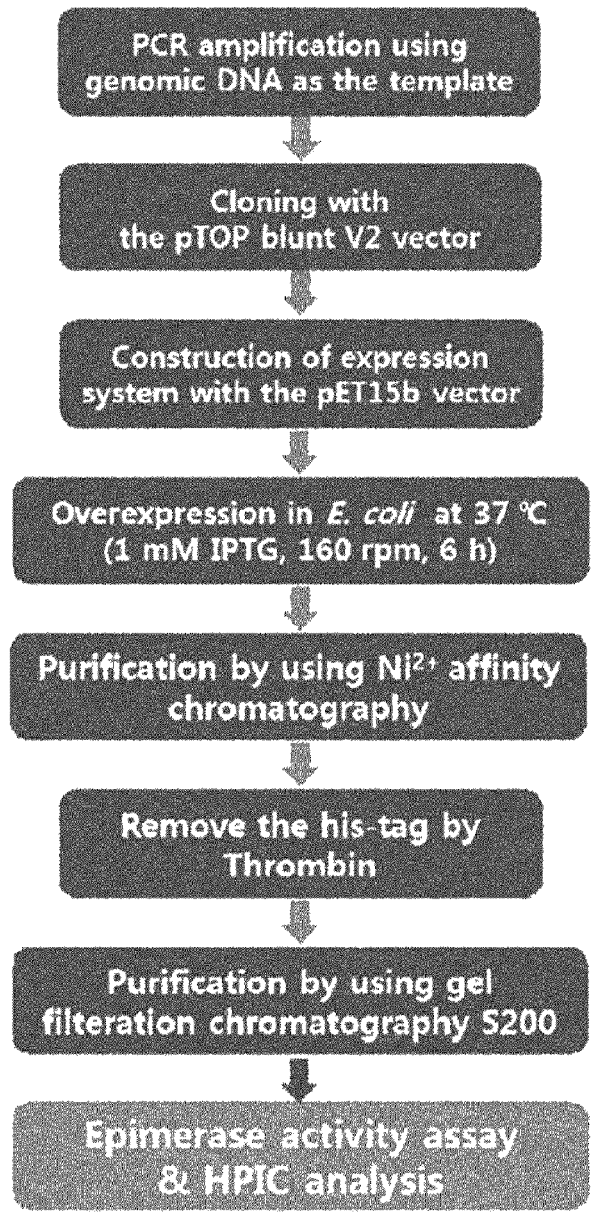

[Fig. 3]
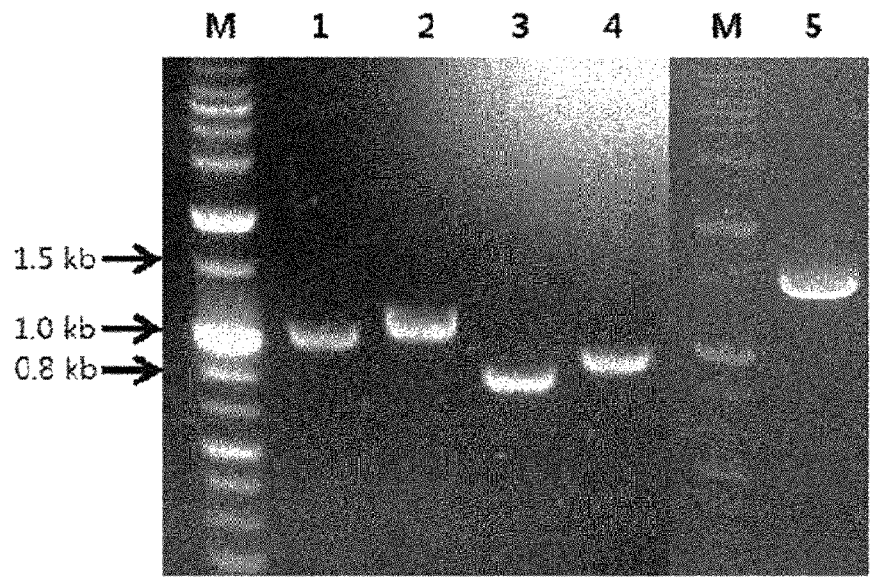
M : DNA size marker
1. A1E, TM0282 (1,071 bp)
2. G2E, TM1034 (1,137 bp)
3. T3E, TM0416 (813 bp)
4. G4E, TM0509 (930 bp)
5. CYTE, (1,452 bp)
[Fig. 4]
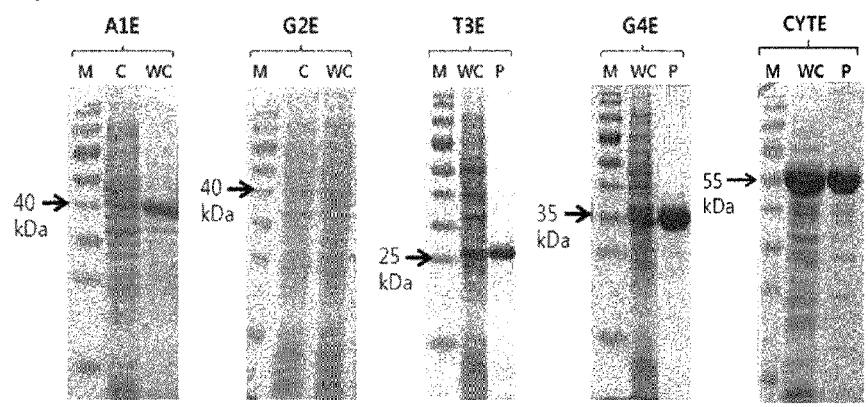

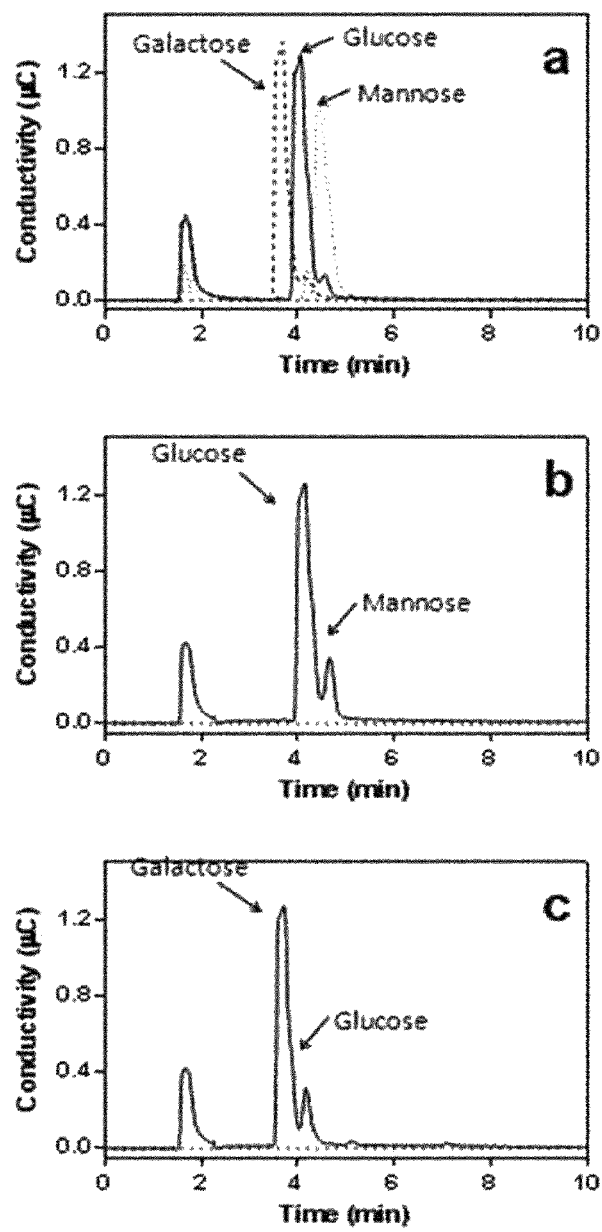
[Fig. 5]

[Fig. 6]
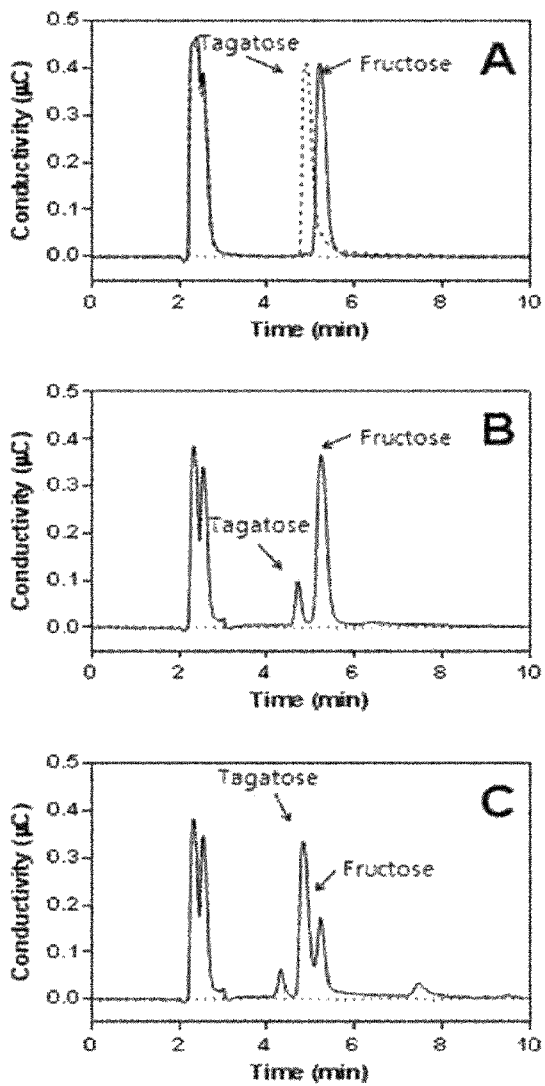
[Fig. 7]
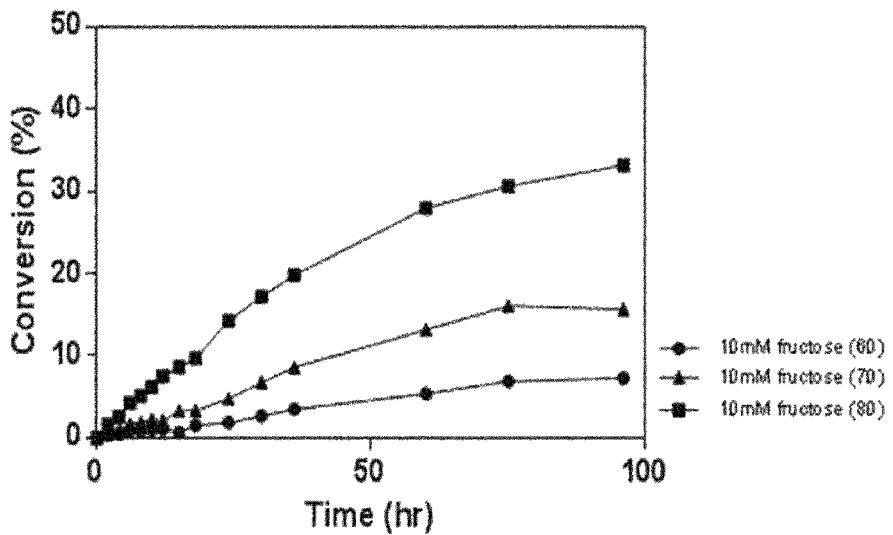

[Fig. 8]
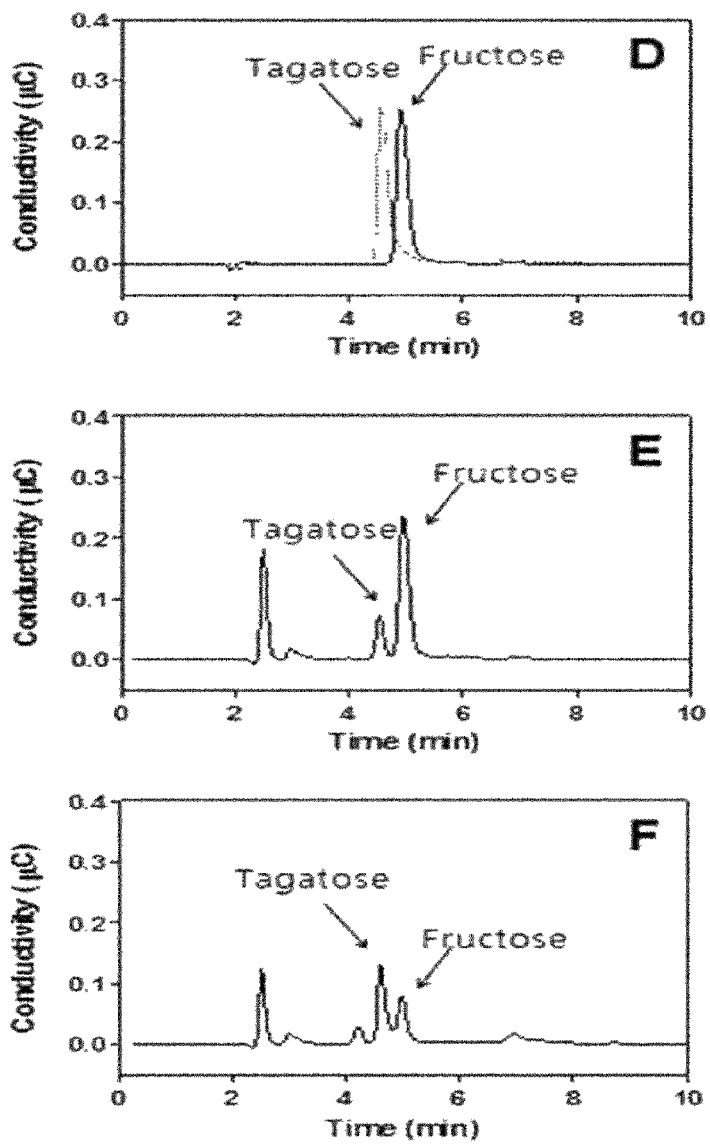
[Fig. 9]
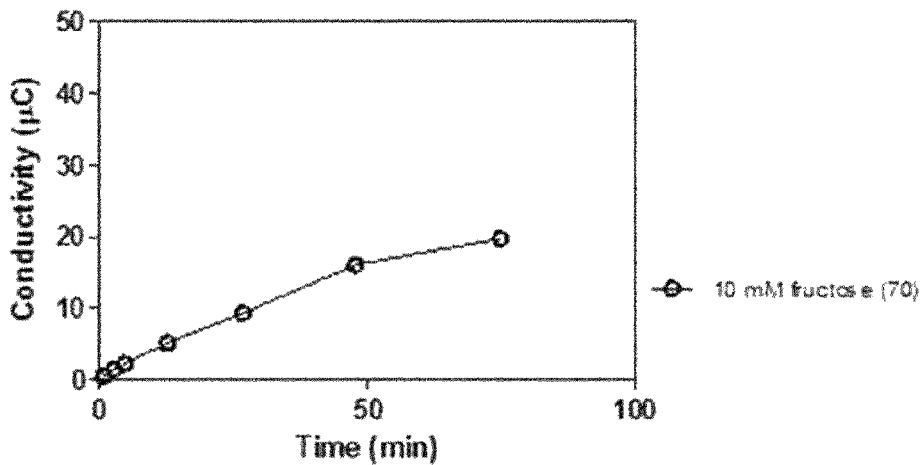

[Fig. 10]
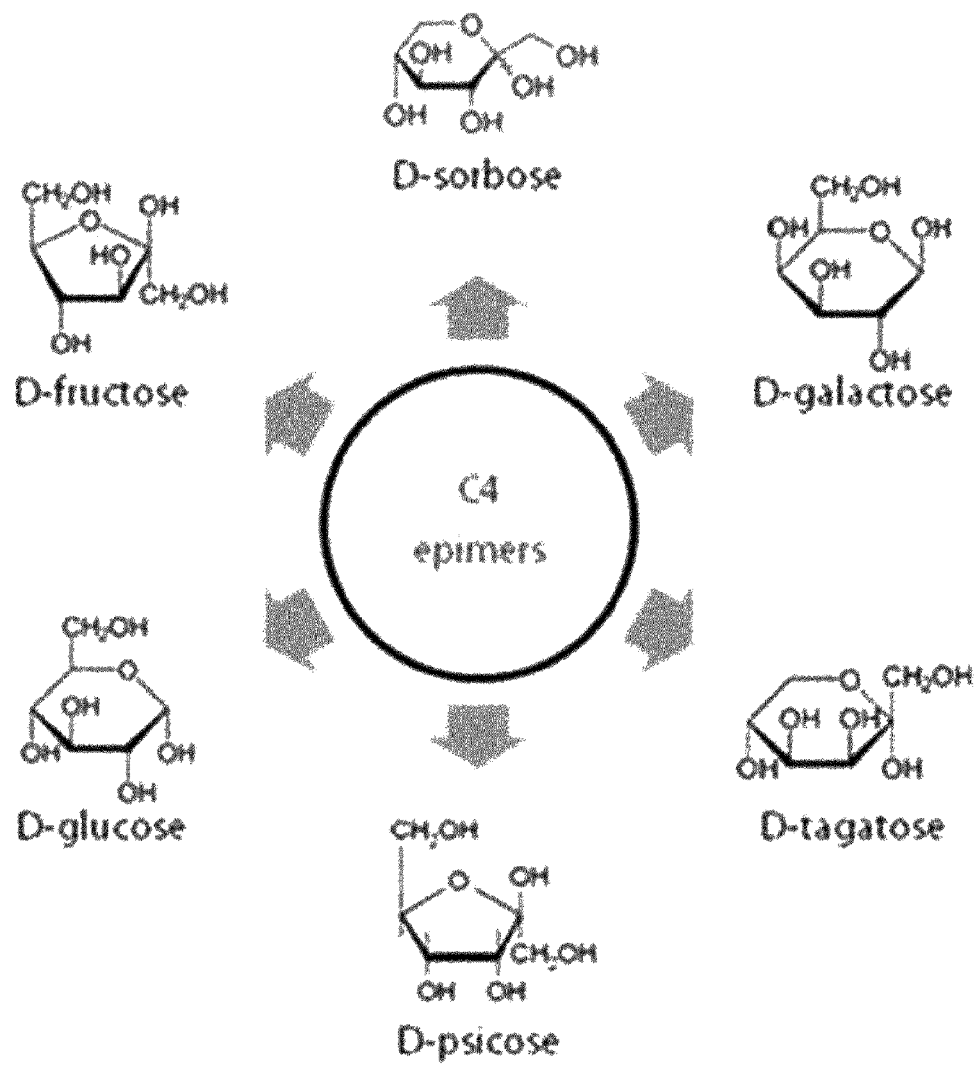

COMPOSITION FOR EPIMERIZATION OF NON-PHOSPHORYLATED HEXOSE COMPRISING SUGAR EPIMERASES DERIVED FROM THERMOPHILES

TECHNICAL FIELD

The present invention relates to a composition for epimerization of non-phosphorylated hexose comprising sugar epimerases derived from thermophiles and a method for preparing a non-phosphorylated hexose epimer using the composition.

BACKGROUND ART

Sweeteners may be defined as flavor enhancers and food additives for a sweet taste, and typically refer to saccharides of carbohydrate excluding dietary fiber and food additives with high sweetness. The most representative sweetener is sugar, and for the past scores of centuries, humans were accustomed to the sweet taste of sugar. Sugar, which is a disaccharide where glucose and fructose are linked by α-1,2 linkage, greatly contributes to processed foods by enhancing flavor, color and gloss, increasing preservability, etc., as well as providing ideal sweetness to foods with lower costs.

However, the major causes for obesity and diabetes, which suddenly increase these days, are associated with an over intake of high calorie foods containing a large amount of sugar according to the improved standards of living. Accordingly, terms 'low-calorie food agent' or 'health functional,' etc., emerge as keywords for new product development in the food industry. Particularly, the efforts to reduce calorie lead to development of sugar substitutes with high sweetness, lower (non) calorie, functionality, and also movement of expansion to global food materialization and commercialization.

Sweetening agents which are substituted with natural sweeteners such as sugar, glucose, and fructose and used for the preparation of processed foods may be classified into (i) high intensity sweeteners (e.g., stevioside, aspartame, etc.), with considerably high relative sugar content, which can contribute to the lowering of calorie, (ii) indigestible non-calorie sweetening agents (e.g., sucralose, etc.), and (iii) functional sweetening agents (e.g., sugar-alcohols such as xylitol, oligosaccharides, etc.), which were developed to satisfy health oriented consumption needs through regulation of risk factors against lifestyle-related diseases. The reports that an over intake of sugar may cause lifestyle-related diseases such as obesity and diabetes, further increase the concerns on these sweetening agent substitutes, which results in expansion and growth of the relevant market. Also, consumers' strong desire for wellbeing, health foods for the purpose of prevention of lifestyle related diseases leads to movement of attempting to apply sweetener substitutes in foods with high sugar content. Accordingly, in Korea, various studies attempting to apply sugar substitutes to processes for preparing confectionery, bakery, rice cake, and beverages are presented on muffins and breads with xylitol added, jellies with functional sugar-alcohols and oligosaccharides added, citrus tea with xylitol and erythritol added, cakes with sweetener substitutes added for diabetes patients, rice cakes with trehalose added, beverages with sweetener substitutes having higher sweetness and lower calorie applied, etc.

Sugar is applied to various foods, while serving in processed foods as not only a sweetener providing a sweet taste, but also a functional agent with physiochemical characteristics which provides preferable properties to final products. In other words, sugar not only provides a sweet taste, but also may (i) provide moisturizing effect to products due to excellent moisture absorbing properties derived from hydroxyl groups, (ii) regulate the properties of starch-containing foods depending on use amount and time during process, and (iii) provide properties and sensual characteristics to products by producing coloring and flavor ingredients by maillard reaction with ingredients containing amino groups and caramelization due to thermal treatment. Thus, the application of sweetener substitutes to processed foods is in need of examination on physiochemical changes in final products and sensual characteristics consumers feel, not simple quantitative substitutes taking into account relative sugar content.

Accordingly, while researching and developing optimization in production of non-phosphorylated hexoses which have drawn attention as a natural, functional sweetener substitute substitutable with existing sweeteners such as sugar, glucose, and fructose, etc., the present inventors confirmed that thermophile-derived sugar epimerases are very effective in epimerization of non-phosphorylated hexoses and completed the present invention.

DETAILED DESCRIPTION OF THE INVENTION

Technical Task

The present invention is to provide a composition for epimerization of a non-phosphorylated hexose comprising sugar epimerases derived from thermophiles Also, another aspect of the present invention is to provide a method for preparing a non-phosphorylated hexose epimer using the composition.

Technical Means for Solving the Technical Task

An aspect of the present invention provides a composition for epimerization of a non-phosphorylated hexose, comprising sugar epimerases derived from thermophiles.

The thermophiles may be from the order Thermotogales.

Also, the sugar epimerase may be at least one selected from the group consisting of aldose-1-epimerase, D-tagatose 3-epimerase, L-ribulose-5-phosphate 4-epimerase, UDP-N-acetylglucosamine 2-epimerase, ribulose phosphate 3-epimerase, nucleotide sugar epimerase, UDP-glucose-4-epimerase, and D-tagaturonate epimerase.

The non-phosphorylated hexose may be an aldohexose or a ketohexose.

The aldohexose may be at least one selected from the group consisting of allose, altrose, glucose, mannose, gulose, idose, talose, and galactose.

The ketohexose may be at least one selected from the group consisting of fructose, psicose, sorbose, and tagatose.

The epimerization may be C-2, C-3, or C-4 epimerization of the non-phosphorylated hexose.

The epimer of the non-phosphorylated hexose may be tagatose or fructose when the sugar epimerase is the order Thermotogales-derived glucose-4-epimerase or D-tagaturonate epimerase.

Also, an aspect of the present invention provides a method for preparing a non-phosphorylated hexose epimer, including treating the non-phosphorylated hexose with the composition for epimerization of the non-phosphorylated hexose.

The non-phosphorylated hexose may be an aldohexose or a ketohexose.

The aldohexose may be at least one selected from the group consisting of allose, altrose, glucose, mannose, gulose, idose, talose, and galactose.

The ketohexose may be at least one selected from the group consisting of fructose, psicose, sorbose, and tagatose.

Advantageous effects

The sugar epimerase derived from thermophiles according to the present invention can effectively catalyze an epimerization reaction of a non-phosphorylated hexose and easily produce an epimer form of the non-phosphorylated hexose, in particular a rare sugar hexose, and thus can be usefully applied in the pharmaceutical and food industry.

BRIEF DESCRIPTION OF DRAWINGS

The above and other features and advantages of the present invention will become more apparent by describing in detail exemplary embodiments thereof with reference to the attached drawing in which:

FIG. 1 is a view showing the genome information of sugar epimerases derived from *T. maritima* and *C. yonseiensis*.

FIG. 2 is a schematic diagram illustrating the overall experimental procedure for examining the epimerization activity of putative non-phosphorylated hexose epimerases with a non-phosphorylated hexose.

FIG. 3 is a view showing the PCR-amplified products of the four genes (TM0282, TM1034, TM0416, and TM0509) encoding putative non-phosphorylated hexose epimerases from *T. maritima* and *C. yonseiensis*.

FIG. 4 is a view showing the SDS-PAGE of the expression of the five genes and purification of the three expressed enzymes (TM0416, TM0509, and CYTE) among them.

FIG. 5 is a BioLC chromatography showing the epimerization products of purified UDP-glucose-4-epimerase with glucose and galactose as substrates.

FIG. 6 is a BioLC chromatography showing the reaction products of purified UDP-glucose-4-epimerase with fructose and tagatose.

FIG. 7 is a view showing the time course of D-tagatose production during UDP-glucose 4-epimerase-catalyzed epimerization of D-fructose at temperature ranging from 60° C. to 80° C.

FIG. 8 is a BioLC chromatography showing the reaction products of purified D-tagaturonate epimerase with fructose and tagatose.

FIG. 9 is a view showing the time course of D-tagatose production during D-tagaturonate epimerase-catalyzed epimerization of D-fructose at; and FIG. 10 is a schematic view showing epimerization of a non-phosphorylated hexose by sugar epimerases derived from thermophiles.

BEST MODE FOR CARRYING OUT THE INVENTION

Hereinafter, the present invention will be described in detail with reference to examples. The examples, however, are provided to illustrate the present invention, and the scope of present invention is not limited to the examples.

EXAMPLE 1

Screening Enzymes for Epimerization of Non-Phosphorylated Hexose

To develop an enzyme that can produce a non-phosphorylated hexose, particularly rare hexose, sugar epimerases derived from *T. maritima* and *C. yonseiensis*, which are thermophiles, were examined

*T. maritima* was obtained according to an obligate anaerobic culture after directly ordering DSMZ 3109 type strain. *C. yonseiensis* was obtained directly by pure isolation from hot water of volcanic district in Indonesia, which was carried out in the laboratory, according to an obligate anaerobic culture.

Specifically, sugar epimerases of *T. maritima* and *C. yonseiensis* are aldose-1-epimerase, D-tagatose 3-epimerase, L-ribulose-5-phosphate 4-epimerase, UDP-N-acetylglucosamine 2-epimerase, ribulose phosphate 3-epimerase, nucleotide sugar epimerase, UDP-glucose-4-epimerase, and D-tagaturonate epimerase. The genetic information of some of the enzymes is as shown in FIG. 1.

The epimerization possibility of the non-phosphorylated hexose was examined based on the genetic information of the above-stated seven enzymes. FIG. 2 is a schematic diagram illustrating an experiment for confirming the enzymes' epimerization activity for the non-phosphorylated hexose.

EXAMPLE 2

Cloning of UDP-glucose-4-epimerase and D-tagaturonate Epimerase Derived from *T maritima* and *C. yonseiensis*

After analyzing the base sequence of a gene encoding UDP-glucose-4-epimerase of *T. maritima* MSB8, primers TM-UDP-glucose 4-epi (NdeI) F: 5'-CATATGAACAT-TCTGGTAACAGGCG-3' and TM-UDP-glucose 4-epi (XhoI) R: 5'-CTCGAGTCACTCAAGGGTTTTTCTG-3' were prepared. PCR was carried out using the primers from the entire gene (genomic DNA) of *T. maritima* MSB8.

After analyzing the base sequence of a gene encoding aldose-1-epimerase of *T. maritima* MSB8, primers TM-aldose 1-epi (Nde I) F: 5'-CATATGGAATATCTGAT-GAGCCACA-3' and TM-aldose 1-epi (BamHI) R: 5'-GGATCCTCAAACTTCAACAGAAAATC-3' were prepared. PCR was carried out using the primers from the genomic DNA of *T. maritima* MSB8.

After analyzing the base sequence of a gene encoding UDP-N-acetylglucosamine 2-epimerase of *T. maritima* MSB8, primers TM-UDP-glucosamine 2-epi (Nde I) F: 5'-CATATGGTGATCAGAGTTCTCAGCG-3' and TM-UDP-glucosamine 2-epi (Xho I) R: 5'-CTCGAGTCA-GCAGAACTCCTCTG-3' were prepared. PCR was carried out using the primers from the genomic DNA of *T. maritima* MSB8.

After analyzing the base sequence of a gene encoding D-tagatose 3-epimerase of *T. maritima* MSB8, primers TM-D-tagatose 3-epi (Nde I) F: 5'-CATATGTTGAAGC-TATCTCTGGTGATC-3' and TM-D-tagatose 3-epi (BamHI) R: 5'-GGATCCTCATGTAAGTTTAATAATCA-GTTC-3' were prepared. PCR was carried out using the primers from the genomic DNA of *T. maritima* MSB8.

After analyzing the base sequence of a gene encoding D-tagaturonate epimerase of *C. yonseiensis* KB-1, primers CY-D-tagaturo epi (Nde I) F: 5'-CATATGATTAACAAAG-TAGCTGAGTATCTTTC-3' and CY-D-tagaturo epi (BamHI) R: 5'-GGATCCTTATTTACTGAATATCTCTT-TAAAGTG-3' were prepared. PCR was carried out using the primers from the genomic DNA of *C. yonseiensis* KB-1.

The PCR reaction solution used is as follows: 100 ng template (obtained genomic DNAs of *T. maritima* MSB8 and *C. yonseiensis* KB-1), 0.5 µl (2.5 units/µl) TaKaRa Prime Star, 10 µl 5× Prime star buffer, 4 µl dNTP mixture (2.5 mM), 0.2 µM (final concentration) each of forward and reverse primer, and up to final volume 50 µl sterile distilled water. PCR was carried out to amplify the genes. PCR reaction was carried out for 30 cycles of denaturation at 95° C. for 1 minute, annealing at 58° C. for 30 seconds, and extension at 72° C. for 1 minute. PCR products were identified as shown in FIG. 3.

With reference to FIG. 3, the amplification products were identified by carrying out electrophoresis in 1% agarose gel. Lane 1 (A1E), lane 2 (G2E), lane 3 (T3E), lane 4 (G4E), and lane 5 (CYTE) refer to PCR amplification products of genes which encode *T. maritima* aldose-1-epimerase (TM0282, 1,071 bp), *T. maritima* UDP-N-acetylglucosamine 2-epimerase (TM1034, 1,137 bp), *T. maritima* D-tagatose 3-epimerase (TM0416, 813 bp), *T. maritima* UDP-glucose-4-epimerase (TM0509, 930 bp), and *C. yonseiensis* D-tagaturonate epimerase (CYTE, 1,452 bp), respectively.

The PCR products were introduced into pTOP Blunt V2 vector (Enzynomics Co., Korea), to prepare vectors pTOPV2-A1E, G2E, T3E, G4E, and CYTE containing genes which encode aldose-1-epimerase, UDP-N-acetylglucosamine 2-epimerase, D-tagatose 3-epimerase, and UDP-glucose 4-epimerase of *T. maritima* MSB8, and D-tagaturonate epimerase of *C. yonseiensis* KB-1, respectively.

Also, after mixing the recombinant vectors with 100 µl competent *E. coli* DH5α prepared for transformation, transformed *E. coli* with the vectors introduced was prepared by heat-shock which was carried out at 42° C. for 45 seconds and spread on LB medium containing 100 µg/ml ampicillin, to screen the transformed *E. coli*.

EXAMPLE 3

Preparation of Recombinant Expression Vectors and Recombinant Strains

To isolate plasmid DNA from the four recombinant vectors pTOPV2-A1E, G2E, T3E, G4E, and CYTE of Example 2, we used the plasmid extraction kit (QIAGEN, USA). For expression of the recombinant enzymes in *E. coli* including UDP-glucose 4-epimerase, the genes of the enzymes, which are TM0282 (A1E), 1034 (G2E), 0416 (T3E), 0509 (G4E), and CYTE, were digested with restriction enzymes NdeI and XhoI or BamHI and ligated into the *E. coli* overexpression vector pET-15b (Novagen, USA) digested with the same restriction enzymes, to prepare recombinant vectors. Subsequently, after mixing the recombinant expression vectors pET-15b-A1E, G2E, T3E, G4E, and CYTE with competent *E. coli* BL21 (DE3) prepared for transformation, transformed *E. coli* with the vectors introduced was prepared by heat-shock which was carried out at 42° C. for 45 seconds and spread on LB medium containing 100 µg/ml ampicillin, to screen the transformed *E. coli*. The trasnsformant *E. coli* was named as "*E. coli* BL21 (D3) pET-15b-A1E, G2E, T3E, G4E, and CYTE (*E. coli* BL21 (DE3) pET-15b-G4E)."

EXAMPLE 4

Expression of Five Enzymes Including Recombinant UDP-glucose 4-Epimerase and D-tagaturonate Epimerase The recombinant *E. coli* strains BL21(DE3) pET-15b-A1E, G2E, T3E, G4E, and CYTE, which were prepared in Example 3 above, were inoculated at 1% (v/v) into the LB medium and cultured at 37° C. for two and a half hours, followed by addition of IPTG to a final concentration of 1 mM to induce expression of the five enzymes including recombinant UDP-glucose 4-epimerase and D-tagaturonate epimerase for 6 hours. To measure the activity of expressed enzymes, the cells were collected by centrifuging the culture medium (10,000×g, 10 minutes) and resuspended in 20 mM Tris-HCl, 0.5 M NaCl, and 5 mM imidazole (pH 7.9). Subsequently, the cells were completely disrupted by sonication, and then fructose epimerization was carried out using it as an enzyme solution. Fructose epimerization was carried out by mixing 1 mg the enzyme solution with 50 mM fructose as the substrate, followed by reaction of 1 ml enzyme reaction solution (20 mM Tris-HCl, pH 7.5) at 80° C. for 3 hours. The reaction products were analyzed on a Bio-LC (Dionex, USA), equipped with ED50 electrochemical detector and Carbo PAC-PA1 column (4×250 mm) A mobile phase (16 mM NaOH) was flowed at a flow rate of 1.0 ml/min D-Tagatose and D-fructose as standards and all the enzyme reaction products were analyzed with the composition described above. D-Tagatose and D-fructose purchased from Sigma were used as the standards and the reaction products by UDP-glucose 4-epimerase and fructose were analyzed. It was confirmed that a certain amount of tagatose was detected.

EXAMPLE 5

Purification of UDP-Glucose 4-Epimerase and D-Tagaturonate Epimerase

To purify the recombinant UDP-glucose 4-epimerase and D-tagaturonate epimerase, which were expressed by the method as in Example 4 above, the recombinant strain culture medium was centrifuged (10,000×g, 10 minutes) to collect only the strains, and the cells were disrupted by sonication, followed by centrifugation at 14,000×g for 20 minutes to remove cell debris and obtain supernatant. Subsequently, the supernatant was heated at 70° C. for 15 minutes and centrifuged at 14,000×g for 20 minutes to remove denaturated *E. coli* protreins and obtain supernatant, followed by $Ni^{2+}$ column chromatography to obtain the recombinant UDP-glucose 4-epimerase (D-tagaturonate epimerase). Thrombin (Novagen, San Diego, USA) digestion was performed to remove hexahistidine attached to N-terminus of the recombinant protein expressed. The treated enzyme solution was loaded onto a HliLoad 16/60 superdex S200 gel column (GE Healthcare).

With reference to FIG. 4, the expression of genes which encode the recombinant aldose-1-epimerase (A1E), UDP-N-acetylglucosamine 2-epimerase (G2E), D-tagatose 3-epimerase (T3E), and UDP-glucose 4-epimerase (G4E), which are derived from *T. maritima*, and D-tagaturonate epimerase (CYTE), which is derived from *C. yonseiensi*, was confirmed with SDS-PAGE analysis. The N-terminal His-tags of G4E and CYTE among these enzymes were removed by Thrombin digestion and finally purified through gel column.

EXAMPLE 6

Analysis of Reaction Products of Purified UDP-glucose 4-Epimerase with Glucose and Galactose The epimerization of glucose and galactose was carried out by mixing an UDP-glucose 4-epimerase (1 mg) solution obtained in Example 5 with 50 mM glucose and galactose each as substrates, followed by reaction of 1 ml enzyme reaction solution (20 mM Tris-HCl, pH 7.5) at 80° C. for 3 hours. The reaction products were analyzed on a Bio-LC (Dionex, USA), equipped with ED50 electrochemical detector and Carbo PAC-PA1 column (4×250 mm) A 16 mM NaOH was used as the mobile phase at a flow rate of 1.0 ml/min. D-Glucose, D-galactose, and D-mannose as standards and all the enzyme reaction products were analyzed as in Example 4. The result is shown in FIG. 5.

FIG. 5 is a view analyzing the reaction products of purified UDP-glucose 4-epimerase with D-glucose and D-galactose through BioLC. 'a' shows the result analyzing standard-D-glucose, D-galactose, and D-mannose through BioLC for identifying the reactants and products of purified UDP-glucose 4-epimerase with D-glucose and D-galactose. 'b' shows the result confirming that D-mannose is detected when D-glucose as the substrate is reacted with purified UDP-glucose 4-epimerase. 'c' shows the result confirming that D-glucose is detected when D-galactose as the substrate is reacted with purified UDP-glucose 4-epimerase. As shown in FIG. 5, it was confirmed that a certain amount of D-mannose is detected when D-glucose as the substrate is reacted with purified UDP-glucose 4-epimerase, and that a certain amount of D-glucose is detected when D-galactose is reacted.

EXAMPLE 7

Analysis of Reaction Products of Purified UDP-glucose 4-epimerase with Fructose and Tagatose The epimerization of fructose and tagatose was carried out by mixing 1 mg purified UDP-glucose 4-epimerase obtained in Example 5 with 50 mM D-fructose and D-tagatose each as substrates, followed by reaction of 1 ml enzyme reaction solution (20 mM Tris-HCl, pH 7.5) at 70° C. for 75 hours. The resulting products were analyzed by Bio-LC (Dionex, USA), equipped with ED50 electrochemical detector and Carbo PAC-PA1 column (4×250 mm) for analysis. A 16 mM NaOH solution was used as the mobile phase at a flow rate of 0.7 ml/min to obtain chromatography. D-Fructose and D-tagatose as standards and all the enzyme reaction products were analyzed as in Example 4. The result is shown in FIG. 6.

FIG. 6 is a view showing the reaction products of purified UDP-glucose-4-epimerase with fructose and tagatose using BioLC. 'a' shows the result analyzing standard-D-fructose and D-tagatose through BioLC for identifying the reactants and products of purified UDP-glucose 4-epimerase with D-fructose and D-tagatose. 'b' shows the result confirming that D-tagatose is detected when D-fructose as the substrate is reacted with purified UDP-glucose 4-epimerase. 'c' shows the result confirming that D-fructose is detected when D-tagatose as the substrate is reacted with purified UDP-glucose 4-epimerase. With reference to FIG. 6, it was confirmed that a certain amount of D-tagatose is detected when D-fructose as the substrate is reacted with purified UDP-glucose 4-epimerase, and that a certain amount of D-fructose is detected when D-tagatose is reacted.

EXAMPLE 8

Production Yield of Tagatose According to Reaction Time Between Purified UDP-glucose 4-Epimerase with Fructose The production yield of tagatose was measured according to reaction (temperature, time) when preparing tagatose from fructose using purified UDP-glucose 4-epimerase obtained in Example 5. 1 mg purified enzyme reaction solution was reacted with 10 mM fructose as the substrate at 60, 70, and 80° C. for 96 hours. Sampling was carried out at times (0, 3, 6, 9, 15, 24, 48, 72, and 96 h) during the reaction for 96 hours to analyze the conversion yield of tagatose. A mixture where 25 µl the reaction solution is mixed with 950 µl distilled water is put into vials (2 ml), and 50 µl the reaction solution as sample was analyzed by Bio-LC (Dionex, USA), equipped with ED50 electrochemical detector and Carbo PAC-PA1 column (4×250 mm) for analysis. A mobile phase (16 mM NaOH) was flowed at a flow rate of 0.7 ml/min in the analysis to obtain chromatography. The result is shown in FIG. 7.

With reference to FIG. 7, when purified UDP-glucose 4-epimerase is reacted with D-fructose, the yield of conversion to D-tagatose increased over reaction time at each temperature, as the temperature increases for 96 hours. Particularly, 30% conversion yield of D-fructose to D-tagatose was reached at 80° C. in 72 hours.

EXAMPLE 9

Analysis of Reaction Products of Purified D-Tagaturonate Epimerase with Fructose and Tagatose The epimerization of fructose and tagatose was carried out by mixing 1 mg purified D-tagaturonate epimerase solution obtained in Example 5 with 50 mM D-fructose and D-tagatose each as substrates, followed by reaction of 1 ml enzyme reaction solution (20 mM Tris-HCl, pH 7.5) at 70° C. for 75 hours. The resulting products were analyzed on a Bio-LC (Dionex, USA), equipped with ED50 electrochemical detector and Carbo PAC-PA1 column (4×250 mm) A mobile phase 16 mM NaOH was flowed at a flow rate of 0.7 ml/min in the analysis to obtain chromatography. Standards of D-fructose and D-tagatose, and all the enzyme reaction samples were analyzed as in Example 4. The result is shown in FIG. 8.

FIG. 8 is a view analyzing the reaction products of purified D-tagaturonate epimerase with D-fructose and D-tagatose using BioLC. 'd' shows the result analyzing standard-D-fructose and D-tagatose through BioLC for identifying the reactants and products of purified D-tagaturonate epimerase with D-fructose and D-tagatose. 'e' shows the result confirming that D-tagatose is detected when D-fructose as the substrate is reacted with purified D-tagaturonate epimerase. 'f' shows the result confirming that D-fructose is detected when D-tagatose as the substrate is reacted with purified D-tagaturonate epimerase. As shown in FIG. 8, it was confirmed that a certain amount of D-tagatose is detected when D-fructose as the substrate is reacted with purified D-tagaturonate epimerase, and that a certain amount of D-fructose is detected when D-tagatose is reacted.

EXAMPLE 10

Time Course of D-Tagatose Production during Purified D-Tagaturonate Epimerase-Catalyzed Epimerization of D-Fructose The production yield of tagatose was measured according to reaction (temperature, time) when preparing tagatose from fructose using purified D-tagaturonate epimerase obtained in Example 5. 1 mg purified enzyme reaction solution was reacted with 10 mM fructose as the substrate at 70° C. for 75 hours. Sampling was carried out at times (0, 1, 3, 5, 13, 27, 48, and 75 h) during the reaction for 75 hours to analyze the conversion yield of tagatose. A mixture where 25 µl the reaction solution is mixed with 950 µl distilled water is put into 2 ml-vials, and 50 µl the reaction solution as sample was analyzed by Bio-LC (Dionex, USA), equipped with ED50 electrochemical detector and Carbo PAC-PA1 column (4×250 mm) A mobile phase 16 mM NaOH was flowed at a flow rate of 0.7 ml/min to obtain chromatography. The result is shown in FIG. 9.

With reference to FIG. 9, when purified D-tagaturonate epimerase is reacted with D-fructose, the yield of conversion to D-tagatose increased over reaction time for 75 hours. Particularly, 19% conversion yield of D-fructose to D-tagatose was reached in 75 hours.

With the above results, sugar epimerase derived from thermophiles is expected to make the epimerization of a non-phosphorylated hexose possible. The expected epimerization is shown in FIG. 10.

MODES FOR CARRYING OUT THE INVENTION

The present invention provides a composition for epimerization of a non-phosphorylated hexose, comprising a thermophile-derived sugar epimerase.

Hereinafter, the present invention is described in detail.

According to the present invention, a thermopile, which is a type of extremophile, is a microorganism that thrives at relatively high temperatures, about 60° C. or higher. The thermopile may preferably be from the order *Thermotogales*, more preferably from the genus *Thermotoga*, the genus *Fervidobacterium*, and the genus *Caldanaerobacter* (previously *Thermoanaerobacter*). According to the present invention, the sugar epimerase refers to an enzyme that catalyzes the epimerization of sugars, i.e., monosaccharides or polysaccharides, by recognizing them as the substrate, and the type thereof is not limited. Preferably, the sugar epimerase may be aldose-1-epimerase, D-tagatose 3-epimerase, L-ribulose-5-phosphate 4-epimerase, UDP-N-acetylglucosamine 2-epimerase, ribulose phosphate 3-epimerase, nucleotide sugar epimerase, UDP-glucose-4-epimerase, and D-tagaturonate epimerase, but is not limited thereto. More preferably, the sugar epimerase may be derived from *Thermotoga maritima* and *Caldanaerobacter yonseiensis*.

The sugar epimerase includes all enzymes naturally occurring or synthesized by a biological or chemical method.

The enzyme may be introduced into a microorganism by a typical method of transformation after obtaining a corresponding gene. The gene of the epimerase may be transformed into a microorganism in the form of a single or a plurality of mutant genes. The microorganism includes prokaryotic and eukaryotic cells, preferably prokaryotic cells. An example of the microorganism is *E. coli*.

According to the present invention, the sugar epimerase derived from thermophiles can effectively derive an epimerization reaction of a non-phosphorylated hexose and easily produce an epimer form of the non-phosphorylated hexose, in particular a rare sugar hexose, and thus can be usefully applied in the pharmaceutical and food industry.

According to the present invention, the non-phosphorylated hexose may be an aldohexose or a ketohexose. The aldohexose may preferably be allose, altrose, glucose, mannose, gulose, idose, talose, or galactose. The ketohexose may be fructose, psicose, sorbose, or tagatose.

According to the present invention, the epimerization may preferably be C-2, C-3, or C-4 epimerization of the non-phosphorylated hexose.

Particularly, when the sugar epimerase is D-tagaturonate epimerase or UDP-glucose-4-epimerase derived from *Thermotoga maritima* or *Caldanaerobacter yonseiensis*, the enzyme may prepare tagatose by epimerizing the non-phosphorylated hexose fructose and fructose by epimerizing tagatose.

Also, the present invention provides a method for preparing a non-phosphorylated hexose epimer, comprising treating a non-phosphorylated hexose with the composition.

According to the present invention, the composition is as defined above.

According to the present invention, the non-phosphorylated hexose may be an aldohexose or a ketohexose. The aldohexose may preferably be allose, altrose, glucose, mannose, gulose, idose, talose, and galactose. The ketohexose may be fructose, psicose, sorbose, and tagatose.

Also, the present invention may provide a method for preparing a polynucleotide encoding sugar epimerase derived from thermophiles, a recombinant vector including the polynucleotide, a host cell transformed with the recombinant vector, and a thermophile-derived sugar epimerase by culturing the host cell.

The term "polynucleotide" refers to a deoxyribonucleotide or ribonucleotide polymer present in the single-stranded or double-stranded form. It includes sequences of genomic RNA, DNA (gDNA and cDNA), and RNA transcribed therefrom. It also includes an analog of natural polynucleotides, unless specifically stated otherwise.

The polynucleotide includes not only a nucleotide sequence encoding sugar epimerase derived from thermophiles, but also a sequence complementary thereto. The complementary sequence includes not only a perfectly complementary sequence, but also a substantially complementary sequence.

Also, the polynucleotide may be modified. The modification includes the addition, deletion or non-conservative or conservative substitution of nucleotide. The polynucleotide encoding amino acid sequence is interpreted to include a nucleotide sequence representing substantial identity with respect to the nucleotide sequence. The substantially identical sequence may refer to a sequence showing at least 60%, at least 70%, at least 80%, at least 90%, or at least 95% identity to the nucleotide sequence, as measured when the nucleotide sequence is aligned to correspond to any other nucleotide sequence as much as possible and the aligned sequence is analyzed using an algorithm generally used in the art. As used herein, the term "vector" refers to a means for expressing a target gene in a host cell. Examples of the vector include plasmid vector, cosmid vector, and virus vector including bacteriophage vector, adenovirus vector, retrovirus vector, and adeno-associated virus vector. A vector that can be used as the recombinant vector may be prepared by manipulating a plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pQE series, pBAD series, pET series, pUC19, etc.), a phage (for example, λgt4λB, λ-Charon, λΔz1, M13, etc.), or a virus (for example, CMV, SV40), which are frequently used in the art.

In the recombinant vector, the polynucleotide encoding a thermophilic sugar epimerase may be operatively linked to a promoter. The term "operatively linked" means a functional linkage between a nucleotide expression regulating sequence (for example, a promoter sequence) and another nucleotide sequence. Thus, the regulating sequence may regulate the transcription and/or translation of another nucleotide sequence.

The recombinant vector may typically be constructed as a vector for cloning or a vector for expression. The vector for expression may be a vector commonly used in the art for expressing foreign proteins in plants, animals or microorganisms. The recombinant vector may be constructed using various methods known in the art.

The recombinant vector may be constructed with a prokaryotic or eukaryotic cell as a host cell. For example, when the vector used is an expression vector, and a prokaryotic cell is used as a host cell, the expression vector used generally includes a strong promoter (for example, $p_L\lambda$ promoter, trp promoter, lac promoter, tac promoter, T5 promoter, T7 promoter, $P_{BAD}$ promoter, etc.) that can proceed with transcription, a ribosome binding site for initiating translation, and a transcription/translation termination sequence. When a eukaryotic cell is used as a host cell, an origin of replication operating in the eukaryotic cell included in the vector includes f1 origin of replication, SV40 origin of replication, pMB1 origin of replication, adeno origin of replication, AAV origin of replication, CMV origin of replication, and BBV origin of replication, etc., but is not limited thereto. Further, a promoter (for example, metallothionein promoter) derived from genomes of mammalian cells or a promoter (for example, adenovirus late promoter, vaccinia virus 7.5K promoter, SV40 promoter, cytomegalovirus (CMV) promoter, and tk promoter of HSV) derived from mammalian viruses may be used. The transcription termination sequence may generally include a polyadenylation sequence.

Meanwhile, the vector may express not only a tumor-targeting peptide of the present invention, but also a fragment of an antibody fused to the peptide or the antibody. In the case of the antibody fused to the peptide or the fragment of the antibody, both a vector system that simultaneously expresses a peptide and an antibody or its fragment in one vector or a vector system that expresses them in separate vectors are possible. In the latter case, two vectors may be introduced into a host cell through co-transformation and targeted transformation.

According to the present invention, any kind of host cell known in the art may be used as a host cell transformed with the recombinant vector. Examples of a prokaryotic cell include strains belonging to the genus Bacillus such as E. coli JM109, E. coli BL21, E. coli RR1, E. coli LE392, E. coli B, E. coli X 1776, E. coli W3110, Bacillus subtilis, or Bacillus thuringiensis, Salmonella typhimurium, and intestinal flora and strains such as Serratia marcescens or various Pseudomonas Spp. When the vector is transformed with a eukaryotic cell, a host cell such as Saccharomyce cerevisiae, an insect cell, a plant cell, and an animal cell, for example SP2/0, CHO (Chinese hamster ovary) K1, CHO DG44, PER. C6, W138, BHK, COS-7, 293, HepG2, Huh7, 3T3, RIN or MDCK cell line may be used.

Another aspect of the present invention may provide a method for preparing a thermophile-derived sugar epimerase, including culturing the host cell.

The polynucleotide or a recombinant vector including the same may be introduced into a host cell using an introduction method widely known in the art. When a host cell is a prokaryotic cell, for example, the delivery may be carried out according to $CaCl_2$ method or electroporation method. When a host cell is a eukaryotic cell, the delivery may be carried out according to microscopic injection method, calcium phosphate precipitation method, electroporation method, liposome-mediated transfection, heat shock, and gene bombardment method, etc., but the delivery method is not limited thereto.

The method for screening the transformed host cell may be readily carried out according to a method widely known in the art using a phenotype expressed by a selected label. For example, when the selected label is a specific antibiotic resistance gene, the transformant may be readily screened by culturing the transformant in a medium containing the antibiotic.

What is claimed is:

1. A method for preparing a non-phosphorylated hexose epimer, the method comprising treating a non-phosphorylated hexose with the composition comprising D-tagaturonate epimerase derived from *Caldanaerobacter vonseiensis* KB-1.

2. The method of claim 1, wherein the non-phosphorylated hexose is an aldohexose or a ketohexose.

3. The method of claim 2, wherein the aldohexose is at least one selected from the group consisting of allose, altrose, glucose, mannose, gulose, idose, talose, and galactose.

4. The method of claim 2, wherein the ketohexose is at least one selected from the group consisting of fructose, psicose, sorbose, and tagatose.

5. The method of claim 1, wherein the non-phosphorylated hexose epimer is a C4epimer.

6. The method of claim 1, wherein the non-phosphorylated hexose is tagatose and the non-phosphorylated hexose epimer is fructose.

7. The method of claim 1, wherein the non-phosphorylated hexose is fructose and the non-phosphorylated hexose epimer is tagatose.

* * * * *

UNITED STATES PATENT AND TRADEMARK OFFICE
CERTIFICATE OF CORRECTION

PATENT NO.         : 9,914,984 B2
APPLICATION NO.    : 15/037274
DATED              : March 13, 2018
INVENTOR(S)        : Dong Woo Lee et al.

Page 1 of 1

It is certified that error appears in the above-identified patent and that said Letters Patent is hereby corrected as shown below:

In the Claims

Please replace "*vonseiensis*" with -- "*yonseiensis*" -- in Claim 1 (Column 12, Line 40).

Please replace "C4epimer" with -- "C4 epimer" -- in Claim 5 (Column 12, Line 52).

Signed and Sealed this
Thirteenth Day of August, 2019

Andrei Iancu
*Director of the United States Patent and Trademark Office*